(12) United States Patent
Calpe Maravilla et al.

(10) Patent No.: US 10,485,420 B2
(45) Date of Patent: Nov. 26, 2019

(54) EYE GAZE TRACKING

(71) Applicant: ANALOG DEVICES GLOBAL UNLIMITED COMPANY, Hamilton (BM)

(72) Inventors: Javier Calpe Maravilla, Alegemesi (ES); Jose Diaz Garcia, Quart de Poblet (ES); Jonathan Ari Goldberg, Lexington, MA (US)

(73) Assignee: ANALOG DEVICES GLOBAL UNLIMITED COMPANY, Hamilton (BM)

( * ) Notice: Subject to any disclaimer, the term of this patent is extended or adjusted under 35 U.S.C. 154(b) by 0 days.

(21) Appl. No.: 15/435,732

(22) Filed: Feb. 17, 2017

(65) Prior Publication Data

US 2018/0235465 A1  Aug. 23, 2018

(51) Int. Cl.

| | |
|---|---|
| *A61B 3/113* | (2006.01) |
| *G02B 27/01* | (2006.01) |
| *G06T 7/73* | (2017.01) |
| *G06T 7/60* | (2017.01) |
| *G06T 7/13* | (2017.01) |
| *G09G 3/02* | (2006.01) |
| *G06T 5/00* | (2006.01) |
| *G06K 9/00* | (2006.01) |

(52) U.S. Cl.
CPC .......... *A61B 3/113* (2013.01); *G02B 27/017* (2013.01); *G06K 9/00597* (2013.01); *G06T 5/006* (2013.01); *G06T 7/13* (2017.01); *G06T 7/60* (2013.01); *G06T 7/73* (2017.01); *G09G 3/02* (2013.01); *G02B 2027/014* (2013.01); *G02B 2027/0138* (2013.01); *G06K 9/00355* (2013.01); *G06T 2207/10028* (2013.01); *G09G 2320/0693* (2013.01)

(58) Field of Classification Search
CPC ...................................................... G06F 3/013
See application file for complete search history.

(56) References Cited

U.S. PATENT DOCUMENTS

| | | | |
|---|---|---|---|
| 5,016,282 A | * | 5/1991 | Tomono ................. G06F 3/013 382/117 |
| 6,433,760 B1 | | 8/2002 | Vaissie et al. |
| 6,659,611 B2 | | 12/2003 | Amir et al. |
| 9,380,287 B2 | | 6/2016 | Nistico et al. |

(Continued)

OTHER PUBLICATIONS

Flávio Luiz Coutinho et al., *Free head motion eye gaze tracking using a single camera and multiple light sources*, XIX Brazilian Symposium on Computer Graphics and Image Processing © 2006 IEEE, 8 pages.

(Continued)

*Primary Examiner* — Phi Hoang
(74) *Attorney, Agent, or Firm* — Patent Capital Group

(57) ABSTRACT

Aspects of the embodiments are directed to systems, methods, and devices for eye gaze tracking. In embodiments, a projective surface, such as a virtual reality display screen or augmented reality projective surface, can project light towards a wearer's eyes. The light can be light representing the shape of the projective surface or can be a displayed shape. The light can be reflected from a cornea. The reflected light from the cornea can be received. A distortion of the shape of the projective surface or displayed shape can be used to determine an eye gaze position.

19 Claims, 11 Drawing Sheets

(56) References Cited

U.S. PATENT DOCUMENTS

| | | | |
|---|---|---|---|
| 2005/0007552 A1* | 1/2005 | Fergason | A61B 3/113 351/210 |
| 2006/0110008 A1* | 5/2006 | Vertegaal | G06K 9/00604 382/103 |
| 2007/0076082 A1* | 4/2007 | Cook | B41J 3/36 347/109 |
| 2010/0053133 A1* | 3/2010 | Furuta | G02B 6/002 345/207 |
| 2013/0114850 A1* | 5/2013 | Publicover | G06K 9/00604 382/103 |
| 2014/0184775 A1* | 7/2014 | Drake | A61B 3/14 348/78 |
| 2015/0289762 A1* | 10/2015 | Popovich | G02B 27/0093 351/209 |
| 2015/0338915 A1* | 11/2015 | Publicover | G06T 19/006 345/633 |
| 2016/0109709 A1* | 4/2016 | Osterhout | G06F 3/03545 359/614 |
| 2016/0309081 A1* | 10/2016 | Frahm | G06F 3/013 |
| 2016/0363995 A1 | 12/2016 | Rougeaux | |
| 2017/0123526 A1* | 5/2017 | Trail | G06F 3/041 |
| 2017/0147859 A1* | 5/2017 | Zhang | G02B 27/0093 |
| 2017/0192499 A1* | 7/2017 | Trail | G06F 3/013 |
| 2017/0263007 A1* | 9/2017 | Cavin | G06T 7/251 |

OTHER PUBLICATIONS

Alexander Plopski et al., *Corneal-Imaging Calibration for Optical See-Through Head-Mounted Displays*, IEEE Transactions on Visualization and Computer Graphics, vol. 21, No. 4, Apr. 2001, 10 pages.

* cited by examiner

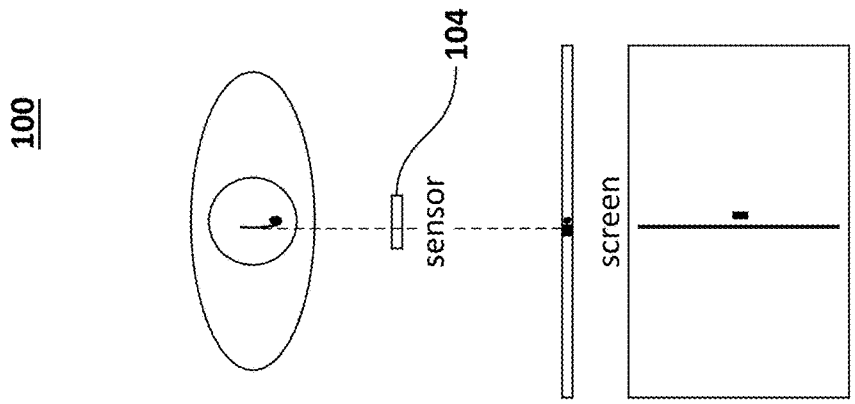
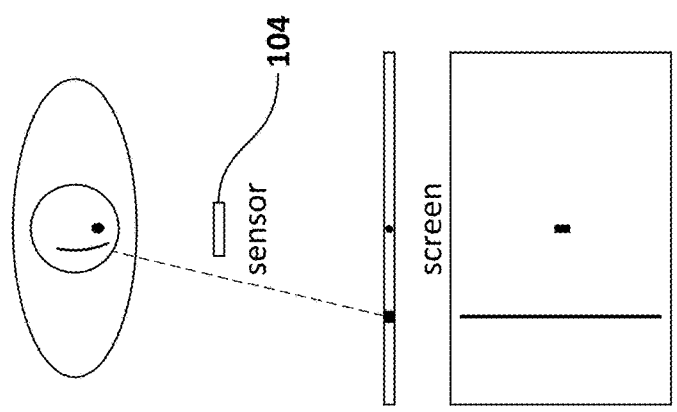
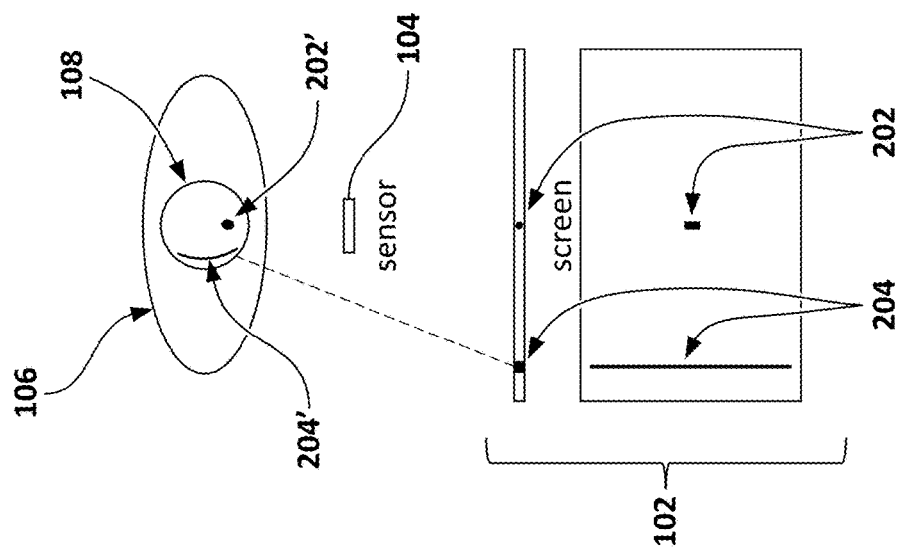

EYE GAZE TRACKING

FIELD

This disclosure pertains to determining the direction of an eye gaze based, at least in part, on reflections from an eye.

BACKGROUND

Eye tracking applications use the position of the eye to determine a direction a user is looking. This is useful in many applications such as Virtual Reality (VR) and Augmented Reality (AR) headsets. Vision based solutions, where a sensor (e.g. a camera or a set of cameras) is included in the frame, can be used to determine eye gaze. A profile of the eye can be reconstructed from images of the eye captured with cameras or similar sensors. Alternatively, light emitting diodes (LEDs) in the near infrared may be used to generate an illumination pattern for studying the position of the glints on the eye and then infer the gaze direction.

SUMMARY

Aspects of the embodiments are directed to a wearable system that includes a projective surface to project an image towards an eye of a wearer; a photo-sensitive element to receive a distorted reflection of the image from the eye of the user; and a processor to determine an eye gaze position based on the distorted reflection of the image.

Aspects of the embodiments are directed to a wearable apparatus that includes a means for projecting an image towards a wearer's eye; a means for detecting a distorted reflection of the image from the wearer's eye; and a processor means for determining an eye gaze position based, at least in part, on the distorted reflection of the projected image from the wearer's eye.

Aspects of the embodiments are directed to a method that includes projecting a shape from a display; receiving a distorted reflection of the projected shape from a portion of a user's eye; and identifying an eye gaze direction based, at least in part, on the distorted reflection of the projected image.

BRIEF DESCRIPTION OF THE DRAWINGS

FIG. 2A is a schematic diagram of a first scanning position of an example calibration process in accordance with embodiments of the present disclosure.

FIG. 2B is a schematic diagram of a first scanning position of an example calibration process in accordance with embodiments of the present disclosure.

FIG. 2C is a schematic diagram of an example calibration process in accordance with embodiments of the present disclosure.

DETAILED DESCRIPTION

Aspects of the embodiments are directed to a system that includes a photodetector, a set of photodetectors, and/or a camera system for eye tracking. In a first example application, a virtual reality (VR) environment (e.g., VR headset) can include a display screen that can provide visual information to a wearer. An example VR headset is described further in FIG. 9. The VR headset can cover a wearer's eyes. The VR headset can include a display screen that allows the wearer to see images displayed by the VR headset. The VR headset can also include a camera, a photodetector (or an array of photodetectors) or other type of light sensor that can detect light reflected off of the wearer's eyes.

The reflections of the display and/or reflections from the display (e.g., objects displayed) can be detected from the surface of the eye. When the eye gaze position changes, the reflection of the objects shown on the display or the display itself shifts because the angle of incidence between the cornea surface and the display changes.

Aspects of the embodiments use the reflected image of a display screen of a VR headset (e.g., VR headset) in order to perform a calibration without additional light-emitting diodes (LEDs) and extra power consumption. The system can use an image sensor with a high dynamic range response (and/or logarithmic response) that provides a large dynamic range, and facilitates the detection of the corneal reflection of the screen.

In embodiments, frames with simple fixed patterns can be inserted within the video stream displayed by the VR headset screen. The fixed patterns can be detected by the image sensor, which can be used for calibration. These patterns can be in the visible range of the spectrum but will not be noticed by the user as they will be on for milliseconds or less. The insertion of these patterns may be random, requested by the eye tracking system and it may be synchronized or not with the video projection subsystem.

In another embodiment we may avoid inserting fixed patterns and use the knowledge we have about the image displayed on the VR goggles or AR glasses. One example would be using the known size of the frame of the information displayed in an AR application.

Figure 1:
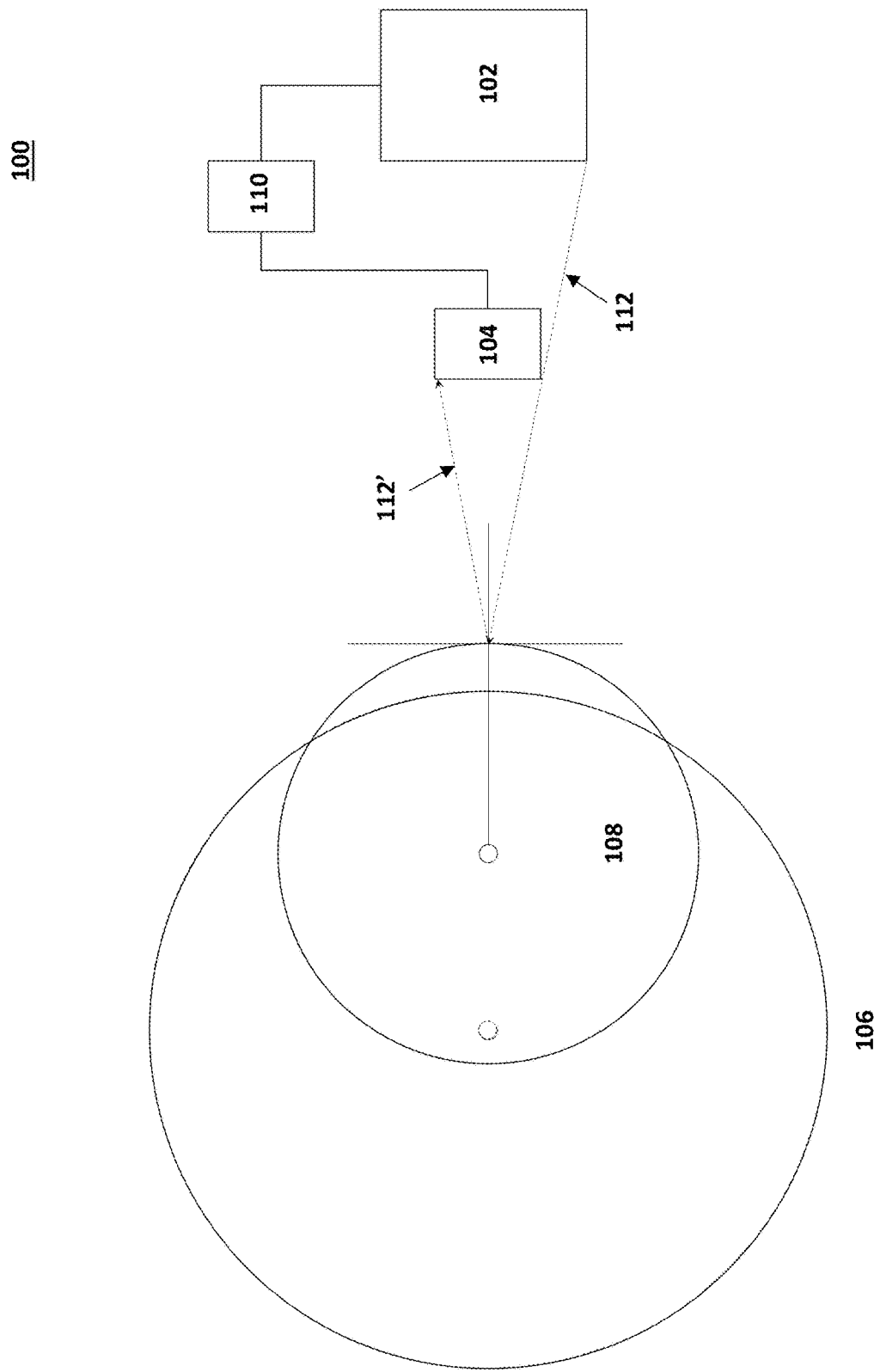
FIG. 1 is a schematic diagram of an example system architecture for eye gaze tracking in accordance with embodiments of the present disclosure.

FIG. 1 is a schematic diagram of an example system architecture 100 for eye gaze tracking in accordance with embodiments of the present disclosure. Example system architecture 100 can be a virtual reality headset, or other system architecture, that includes a display screen 102. Display screen 102 can display images to a user/wearer. The display screen 102 can be at a known distance from the wearer, or more specifically, from an eye of the wearer. The known distance can be a substantially fixed distance from the wearer, in the case of VR headset implementations and AR headset implementations.

The system architecture 100 can include an image sensor 104. The image sensor 104 can detect reflections from eye 106. The image sensor may have a logarithmic response that provides a large dynamic range, and facilitates a detection of a corneal reflection of the display screen 102 without dedicated lighting. The eye 106 includes a cornea 108. The cornea 108 can reflect light emitted from the display screen 102. The reflected light can be detected by the image sensor 104. A processor 110 can use the shapes, as reflected from the cornea 108, to determine its position and therefore the direction that the eye is pointing (i.e., an eye gaze direction).

At the outset, a calibration can be used to relate the geometry of the system architecture 100 with respect to the external world in an AR application and calibrate the effects of the small geometry changes in the system both in AR and VR applications. Calibration allows a fast, autonomous, non-supervised recalibration any time a user puts on the headset again or there are goggle motions during their use. Put differently, the calibration process described herein can be performed at start-up for any wearer, and can be performed periodically (or as needed) during operation of the headset.

FIGS. 2A-2C are schematic diagrams of an example calibration process in accordance with embodiments of the present disclosure. The calibration processes uses the same or similar system architecture as that shown in FIG. 1. The display 102 can display a single point 202 to a wearer, who is to gaze at the single point 202 for the duration of the calibration. A reference line or other shape is scanned across the screen while the eye gaze is fixed at the point 202. Scanning may be performed by generating a (bright colored or white) line pattern 204 on the (black or dark) screen 102 and moving the line pattern 204 across the screen 102. The light emitted by line pattern 204 can reflect off of the cornea 108 of eye 106 (the process can be performed for each eye of the wearer). Reflections 204' of the line pattern 204 are detected by sensor 104 as the line pattern 204 scans across the screen 102. For example, reflection 204' can be detected by sensor 104. In embodiments, a reflection 202' of gazing point 204 can also be detected by sensor 104. A processor, such as processor 110, can form a 3D structure of the eye as it is gazing at that gazing point 202. By adding more gazing points, accuracy can be improved. For example, the wearer can first gaze at a first gazing point for a first calibration cycle. The wearer can then gaze at a second gazing point, and a line pattern can be scanned across the display. Reflections of the line pattern reflected from the eye while the eye is gazing at the second gazing point (e.g., the eye is in a second gazing position) can be detected by sensor 104. The processor can form a 3D structure from the detected reflections of the line patterns for the second eye gaze position. This process can be repeated for as many gazing points are implemented (e.g., based on a level of accuracy desired by implementation choice).

The 3D structure of the eye can be used as a baseline for calibration purposes. The eye surface contours can be mapped, and the contours can be correlated to an eye position using the gazing pattern and scanned patterns.

In embodiments, a two dimensional pattern can be used, as opposed to (or in addition to) a linear pattern. A two-dimensional pattern can be a rectangular shape that is distorted depending on the eye gaze position. The distortion of a rectangular pattern can be correlated to an eye gaze position. The system can learn about how the rectangular pattern distorts, and such distortions can be used to train the system. Other patterns can also be used.

Figure 3:
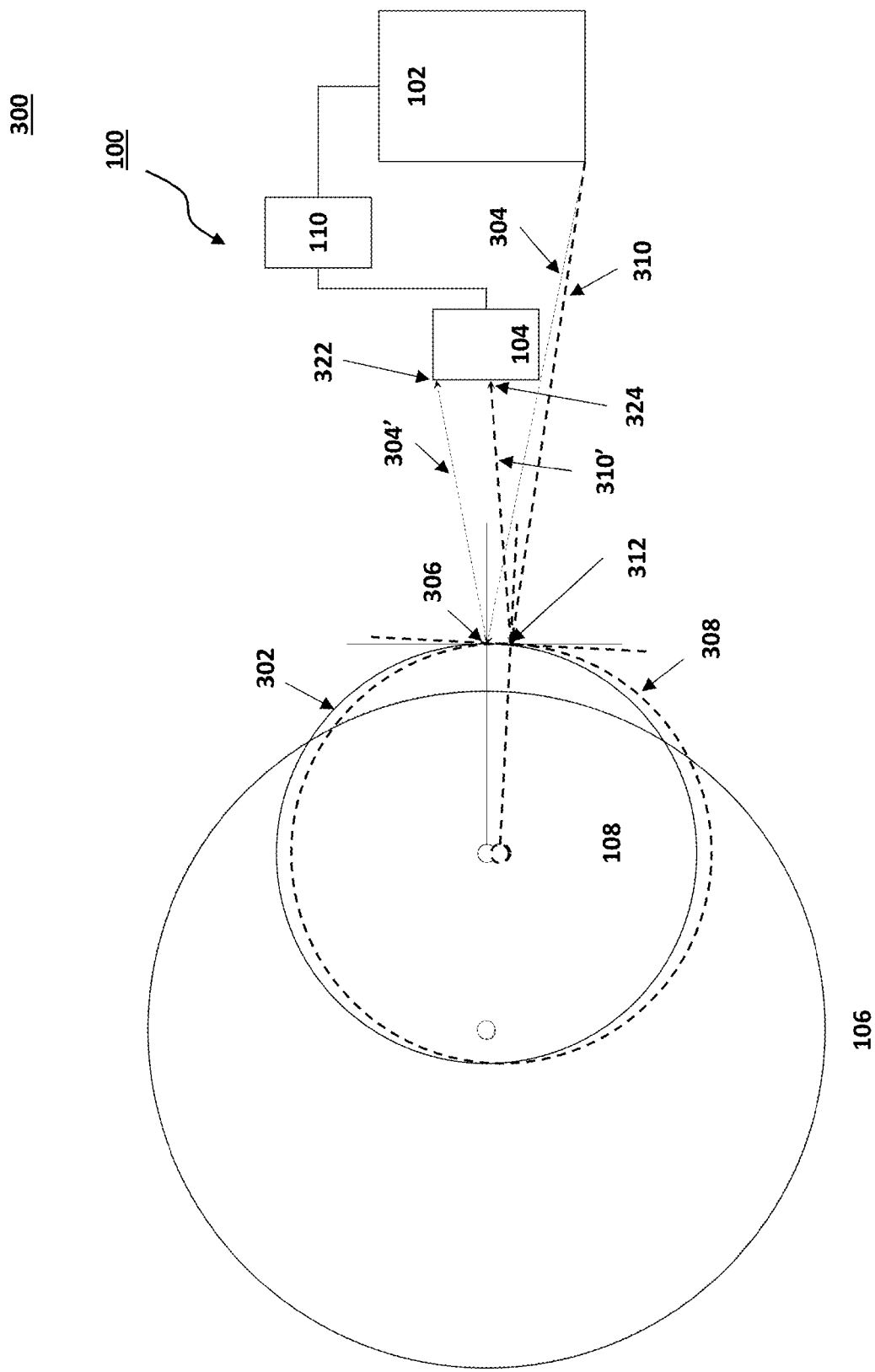
FIG. 3 is a schematic diagram of the system architecture of FIG. 1 illustrating a change in eye position in accordance with embodiments of the present disclosure.

FIG. 3 is a schematic diagram of the system architecture of FIG. 1 illustrating a change in eye position in accordance with embodiments of the present disclosure. FIG. 3 shows the eye 106 in a first position 302. In the first position 302, the cornea 108 can receive light 304 from the display 102 at a point 306 on or near the cornea 108 (i.e., the sclera is continuous with the cornea). The light 304 is reflected (shown as reflected light 304') to a first point 322 on the image sensor 104. The reflected light 304' can be resolved into an image representative of the screen 104, and the shape of the resolved image can be used to determine an eye gaze position.

When the eye gaze position changes to a second position 308, light 310 emitted from the display 102 impinges on point 312 on or near the cornea 108. Reflected light 310' is received at the image sensor 104 at a point 324, different from point 322. The received reflected light 310' can be resolved into an image of the display screen 102, and the shape of the resolved image can be used to determine another eye gaze position.

Figure 4A:
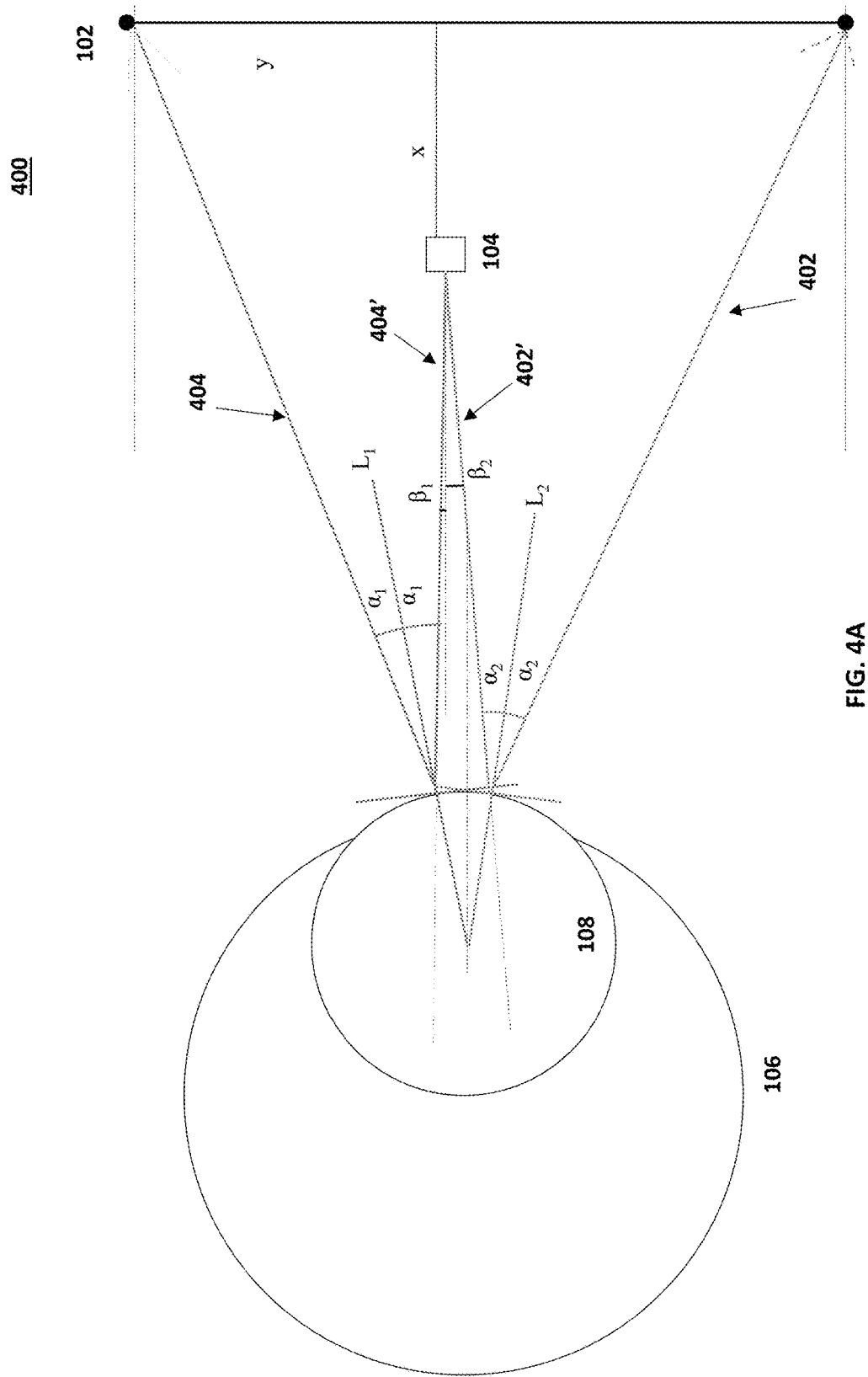
FIGS. 4A-B are schematic diagram of the system architecture of FIG. 1 illustrating example angles of incidence and reflections in accordance with embodiments of the present disclosure.
Figure 4B:
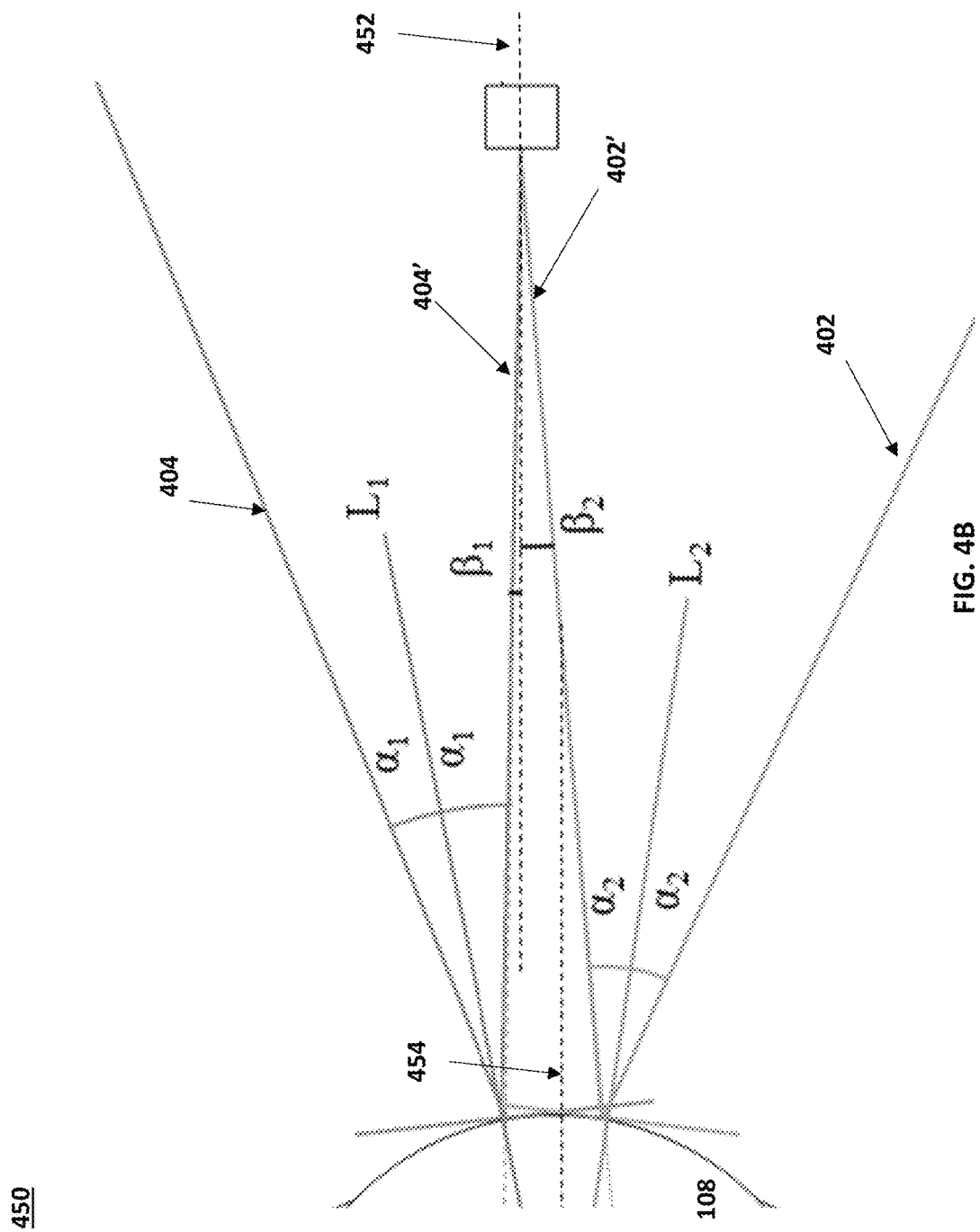

FIG. 4A is a schematic diagram of the system architecture of FIG. 1 illustrating example angles of incidence and reflections in accordance with embodiments of the present disclosure. FIG. 4B is a schematic diagram of a close-up view of the system architecture of FIG. 4A illustrating example angles of incidence and reflections in accordance with embodiments of the present disclosure. Light from the display 102 representative of the screen frame, a displayed scene, one or more calibration points, etc. is emitted from a display screen 102 (or AR reflective lens) that is at a known distance from the wearer (to a certain percent error). A sensor 104 is located at a known distance from the wearer and from the display 102. Light, such as light 402 or light 404, is emitted from the display 102. Since the cornea 108 is a sphere or is near spherical (shown as a circle in a 2D simplification), incident and reflected light beams have the same angle ($\alpha$) with respect to a line (L) from the center of the circle to the incident point. The reflected light 402' and 404' is received at the sensor 104 in a known angle ($\beta1$ and $\beta2$) relative to a normal to the sensor, having been reflected on the cornea 108. The angles of incidence $\beta1$ and $\beta2$ are shown in more detail in FIG. 4B.

Figure 5:
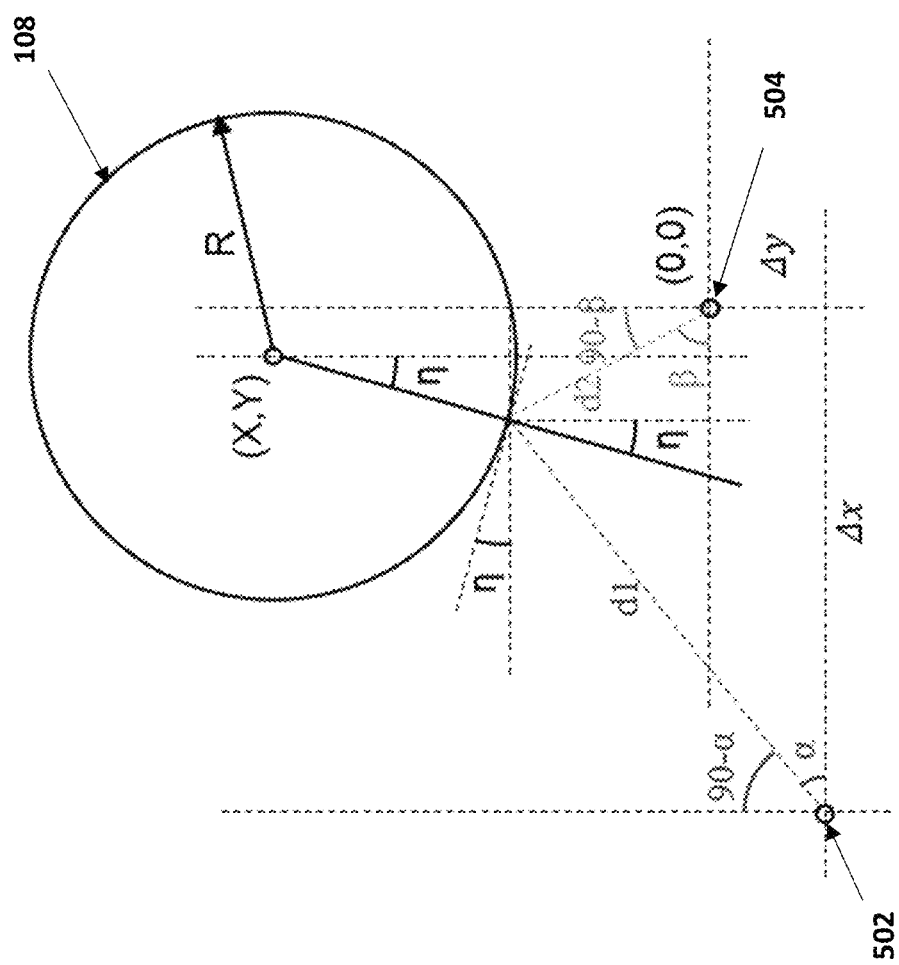
FIG. 5 is a schematic diagram of a cornea reflecting light from a point source on a display towards a point on a display in accordance with embodiments of the present disclosure.

FIG. 5 is a schematic diagram of a cornea 108 reflecting light from a point source 502 on a display towards a point 504 on an image sensor in accordance with embodiments of the present disclosure. FIG. 5 provides one example scenario for resolving a shape and size of the reflection from the cornea 104 physio-metrically. A relationship between the angle of light emission $\alpha$ and the angle of light reception at the image sensor $\beta$ can be determined:

$$90-\alpha-\eta=90-\beta+\eta \rightarrow \alpha=\beta-2*\eta$$

These relationships for the $\alpha$ and $\beta$ can be further resolved into spatial dimensions:

$$\sin(\alpha)*d1-\sin(\beta)*d2=\Delta y$$

$$\cos(\alpha)*d1+\cos(\beta)*d2=\Delta x$$

$$\sin(\beta)*d2+\cos(\eta)*R=Y$$

$$\cos(\beta)*d2+\sin(\eta)*R=X$$

The image sensor point can be considered at an origin (0,0). A shift in eye gaze can place the focus of the cornea to a point (X,Y). The value of R can be approximated to a value between 6 and 7 mm, such as 6.7 mm.

This example assumes a single point source of light emission from the display 104. The relationships can be resolved for more than one point source of light emission in a similar way, and can improve resolution of various aspects of the resolved image generated from the received reflected light.

A 3D model of the eye can be formed to determine the eye gaze position (e.g., based on a correlation from the calibration).

Figure 6A:
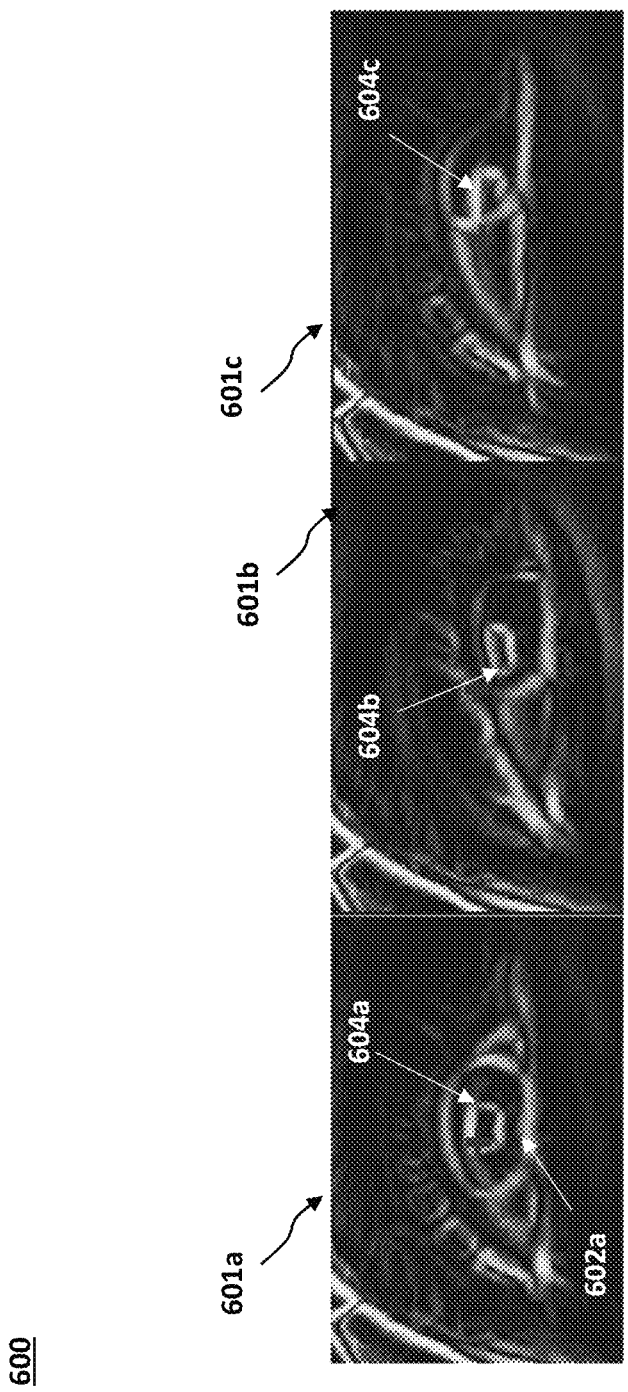
FIG. 6A is a diagram illustrating example reflections of a screen from a cornea in accordance with embodiments of the present disclosure.

FIG. 6A is a diagram 600 illustrating example images of reflections of a screen from a cornea in accordance with embodiments of the present disclosure. As mentioned previously, a reflection from a display screen from a cornea 602 can be used to form an image 604 of the display screen (or scene shown on the display screen or other display screen features, such as a frame of the screen). In images 601a-601c, the eye is shown to move its gaze towards the right of the page. In image 601a, the eye is gazing substantially forward, by example. The display screen image 604 can have a shape that indicates that the eye is gazing forward. In image 601b, the eye gaze position has shifted to the wearer's left, and the observer's right. The display screen image 604b is shown to be different that the image 604a. The shape of image 604b can be characterized in a manner similar to that described in FIGS. 4A-B and FIG. 5 to determine the eye gaze position. Similarly, in image 601c, the eye gaze position has shifted further to the wearer's left, and the observer's right. The display screen image 604c is shown to be different that the images 604a and 604b.

The gaze direction can be identified by how a rectangular frame (e.g., a frame of a display or an image displayed) gets distorted. Depending of the curvature of the eye at the reflection area, the distortion of the rectangular frame will be different (as described above in FIG. 6A). The distortion can be used to obtain the gaze direction and/or train a system.

Figure 6B:
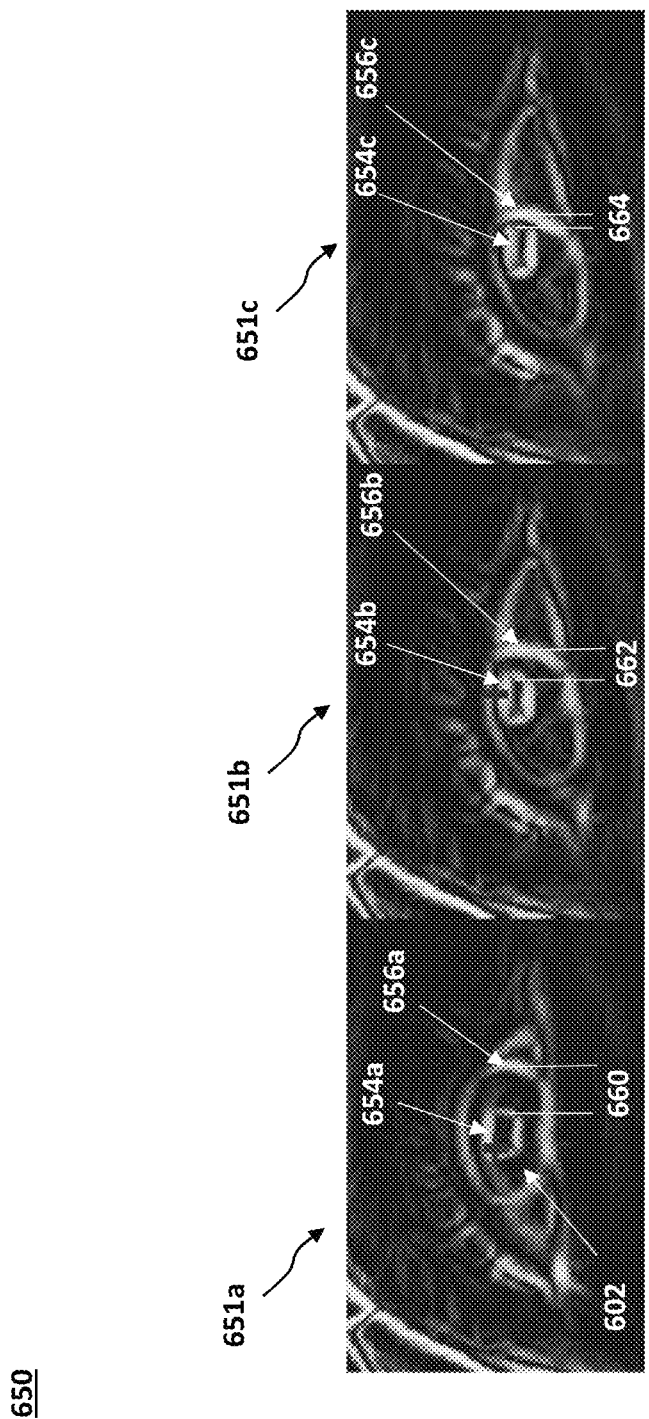
FIG. 6B is a diagram illustrating another example of reflections of a screen from a cornea in accordance with embodiments of the present disclosure.

FIG. 6B is a diagram 650 illustrating example reflections of a screen from a cornea in accordance with embodiments of the present disclosure In addition to imaging the reflection of the display screen, other reflections can be used to characterize the direction of eye gaze. For example, in image 651a, a reflection of the outline of the cornea 602 is resolved into an image 656a. The outline image 656a can be used to compare the relative position of the display image 654a. A distance 660 between the outline image 656a and the image of the display screen 654a can be determined to identify a direction of eye gaze. In image 651b, the eye gaze has moved to the wearer's right, observer's left. The distance 662 between the outline image 656b and the display screen image 654b has decreased. Similarly, in image 651c, the eye gaze has moved to the wearer's right, observer's left. The distance 664 between the outline image 656c and the display screen image 654c has decreased further. The relative position of the reflections of the display screen to the outline images can be used to obtain eye gaze direction.

Figure 7:
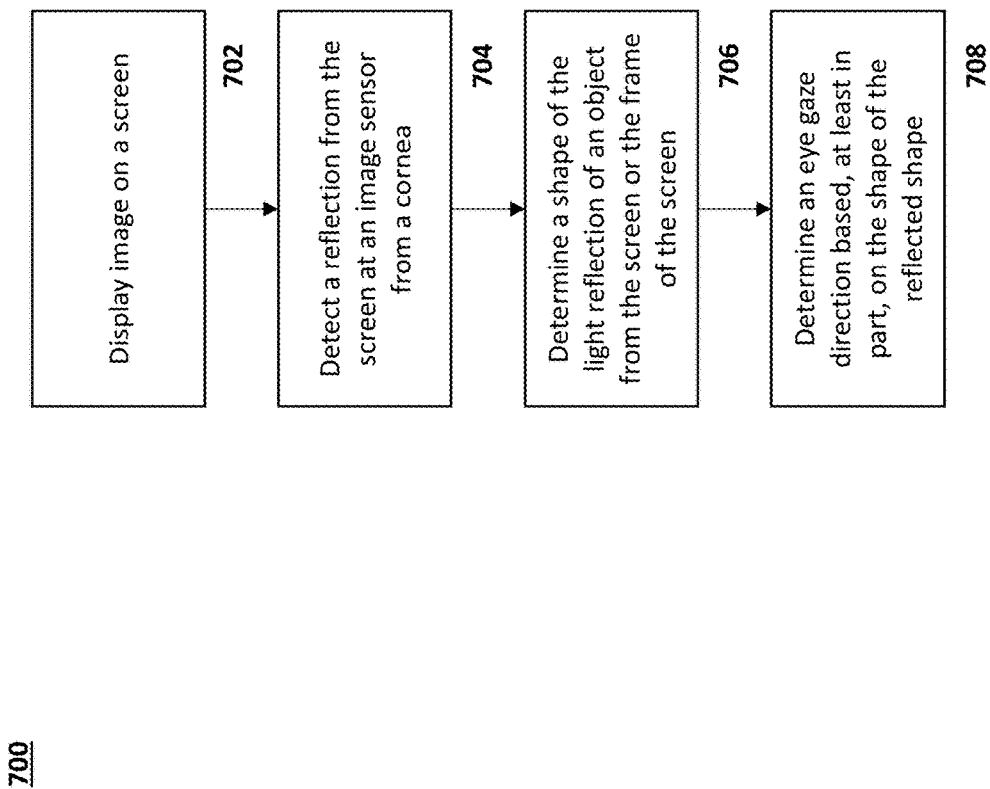
FIG. 7 is a process flow diagram for determining eye gaze position in accordance with embodiments of the present disclosure.

FIG. 7 is a process flow diagram for determining eye gaze direction in accordance with embodiments of the present disclosure. At the outset, an image can be displayed on a screen (702). The screen can be a display screen of a VR headset, AR headset, a computer screen, smartphone, etc. The image can be a calibration image, an actual VR image, or other image. An image sensor, such as that of a camera or other imaging system, can detect a reflection of the light emitted from the display screen that is reflected from a cornea of an eye of the user/wearer (704). A shape of the detected reflected light can be resolved into an image (706). An eye gaze direction can be determined based, at least in part, on the shape of the detected reflected light (708).

Figure 8:
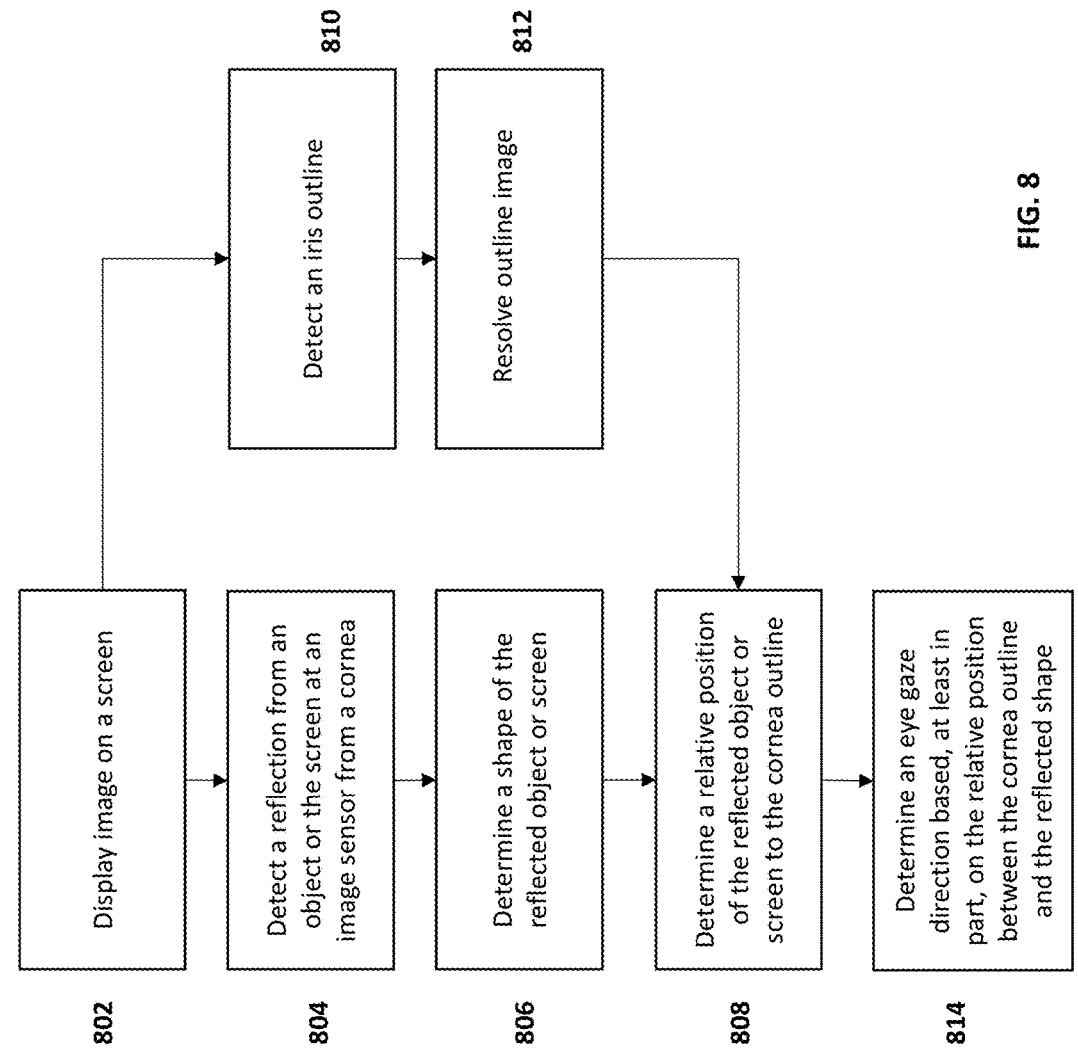
FIG. 8 is a process flow diagram for tracking eye gaze in accordance with embodiments of the present disclosure.

FIG. 8 is a process flow diagram for tracking eye gaze in accordance with embodiments of the present disclosure. At the outset, an image can be displayed on a screen (802). An image sensor, such as that of a camera or other imaging system, can detect a reflection of the light emitted from the display screen that is reflected from a cornea of an eye of the user/wearer (804). The image sensor can also detect light emitted from the display that is reflected from other areas of the eye, and detect features such as the outline of the iris (810). A shape of the detected reflected light can be resolved into an image (806). The reflected light from the outline of the iris can also be resolved into an image (812). A relative position between the iris outline image and the reflected screen image can be determined (808). An eye gaze direction can be determined based, at least in part, on the relative position of the reflected screen image and the outline image of the iris (814).

Figure 9:
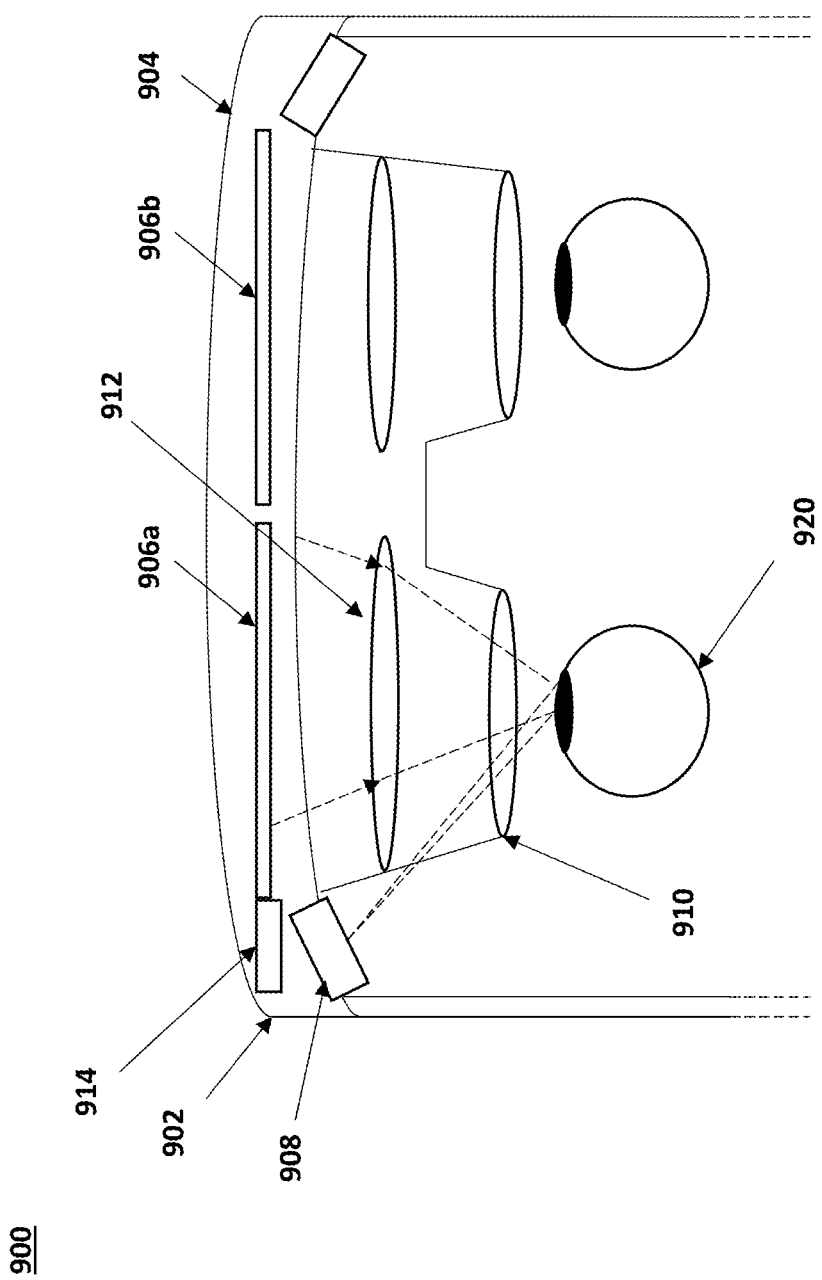
FIG. 9 is a schematic diagram of an example virtual reality headset in accordance with embodiments of the present disclosure.

FIG. 9 is a schematic diagram of an example virtual reality headset 900 in accordance with embodiments of the present disclosure. The VR headset 900 includes a frame 902 that supports a display housing 904 and one or more photodetector elements 908. The display housing 904 can house display units 906a and 906b that are configured to display or project images to a wearer. The photodetector element 908 can detect reflected light from the wearer's eyes 920. The photodetector element 908 can be an image sensor, such as an image sensor with a high dynamic range response. The VR headset can also include a lens housing 910 that directs and focuses displayed light towards the wearer's eyes 920. The lens housing 910 can include one or more lenses 912. The VR headset can include a processor 914, such as a hardware processing unit. The processor 914 can include a central processor, a graphics processor, memory, etc. The processor 914 can control the display to project eye gaze calibration points or grids or patterns for calibration, VR content, etc. The processor 914 can also intermittently project calibration patterns within frames of VR content for occasional recalibration.

The processor 914 can also process reflected light received by the image sensor to determine eye gaze. The processor 914 can determine eye gaze by determining a distortion of a pattern, such as a two dimensional pattern reflected from the eye 920. The two dimensional pattern can be the frame of the display 906a, an image projected from the display 906a, etc.

The processor 914 can also form three dimensional models of the eye based on the reflections of patterns received at the image sensor. The three dimensional models of the eye can be formed to increase the accuracy of the eye gaze position estimation by mapping the contours of the eye. The three dimensional model of the wearer's eye can be used to understand how a reflection of a linear pattern or two dimensional shape will distort as the eye changes gazing position.

What is claimed is:

1. A wearable apparatus which projects a native image onto a wearer's eye and determines eye gaze tracking by analyzing a reflection from the wearer's cornea, the wearable apparatus comprising:
   a display which projects the native image;
   an image sensor which receives the reflection of the native image; and,
   a processor in electrical communication with the image sensor and the display, the processor configured to:
   receive data representative the native image;
   receive data representative of the reflection of the native image;

compare the data representative of the native image with the reflection of the native image;

detect distortions of the data representative of the native image with the reflection of the native image;

resolve the distortions of the data representative of the native image with the reflection of the native image into a reflected shape; and, determine eye gaze based upon the distortions and reflected shape;

wherein, the distortion detection does not rely upon any light other than the reflection of the native image.

2. The wearable apparatus of claim 1, wherein the wearable apparatus is comprised by one of a virtual reality display screen and an augmented reality headset projector.

3. The wearable apparatus of claim 1, wherein the image sensor comprises high dynamic range image sensor.

4. The wearable apparatus of claim 1, wherein the processor is further configured to:

determine a first edge of the reflected shape;

determine a second edge of the reflected shape;

compare the first edge to the second edge of the reflected shape; and wherein, identify eye gaze direction based, at least in part, upon the first and second edge of the reflected shape.

5. The wearable apparatus of claim 4, further comprising a circuit providing edge detection.

6. The wearable apparatus of claim 1, wherein the identification of eye gaze direction is based solely on the distorted reflection of the projected native image and not on gridlines, beacons, image markers, not light outside the bandwidth of the native image.

7. The wearable apparatus of claim 1, the processor further configured to:

intermittently display a calibration image on the display;

receive a reflection of the calibration image at the image sensor;

determine a shape of the calibration image; and correlate the shape of the calibration image to an eye gaze direction.

8. A method for determining eye gaze in a wearable apparatus by projecting a native image onto a wearer's eye and analyzing a reflection from the wearer's cornea, the method comprising:

displaying a scene comprised by the native image;

sensing a reflected image on an image sensor;

electrically communicating data representative of the reflected image to a processor;

receiving data representative, the native image at the processor;

receiving data representative of the reflection of the native image at the processor;

comparing the data representative of the native image with the reflection of the native image;

detecting distortions of the data representative of the native image with the reflection of the native image;

resolving the distortions of the data representative of the native image with the reflection of the native image into a reflected shape; and, determining eye gaze based upon the distortions and reflected shape;

wherein, the scene contains no beacons, gridlines, nor specific image locators.

9. The method of claim 8, wherein the wearable apparatus is comprised by one of a virtual reality display screen and an augmented reality headset projector.

10. The method of claim 8, wherein the image sensor comprises high dynamic range image sensor.

11. The method of claim 8, further comprising:

determining a first edge of the reflected shape;

determining a second edge of the reflected shape;

comparing the first edge to the second edge of the reflected shape; and wherein, identify eye gaze direction based, at least in part, upon the first and second edge of the reflected shape.

12. The method of claim 8, wherein the identification of eye gaze direction is based solely on the distorted reflection of the projected native image and not on gridlines, beacons nor image markers.

13. The method of claim 8, further comprising:

intermittently displaying a calibration image on the display;

receiving a reflection of the calibration image at the image sensor;

determining a shape of the calibration image; and correlating the shape of the calibration image to an eye gaze direction.

14. A wearable apparatus which projects a native image onto a wearer's eye and determines eye gaze tracking by analyzing a reflection from the wearer's cornea, the wearable apparatus comprising:

means for displaying a scene comprised by the native image;

means for sensing a reflected image on an image sensor;

means for electrically communicating data representative of the reflected image to a processor;

means for receiving data representative the native image at the processor;

means for receiving data representative of the reflection of the native image at the processor;

means for comparing the data representative of the native image with the reflection of the native image;

means for detecting distortions of the data representative of the native image with the reflection of the native image;

means for resolving the distortions of the data representative of the native image with the reflection of the native image into a reflected shape; and, means for determining eye gaze based upon the distortions and reflected shape;

wherein, the scene contains no beacons, gridlines nor specific image locators.

15. The wearable apparatus of claim 14, wherein the wearable apparatus is comprised by one of a virtual reality display screen and an augmented reality headset projector.

16. The wearable apparatus of claim 14, wherein the image sensor comprises high dynamic range image sensor.

17. The wearable apparatus of claim 14, further comprising:

means for determining a first edge of the reflected shape;

means for determining a second edge of the reflected shape;

means for comparing the first edge to the second edge of the reflected shape;

and wherein, means for identifying eye gaze direction based, at least in part, upon the first and second edge of the reflected shape.

18. The wearable apparatus of claim 14, wherein the identification of eye gaze direction is based solely on the distorted reflection of the projected native image and not on gridlines, beacons, nor image markers.

19. The wearable apparatus of claim 14, further comprising:

means for receiving a reflection of the calibration image at the image sensor;
means for determining a shape of the calibration image; and
means for correlating the shape of the calibration image to an eye gaze direction.

\* \* \* \* \*